United States Patent [19]

Casey et al.

[11] 4,452,973
[45] Jun. 5, 1984

[54] POLY(GLYCOLIC ACID)/POLY(OXYETHYLENE) TRIBLOCK COPOLYMERS AND METHOD OF MANUFACTURING THE SAME

[75] Inventors: Donald J. Casey, Ridgefield; Mark S. Roby, Stamford, both of Conn.

[73] Assignee: American Cyanamid Company, Stamford, Conn.

[21] Appl. No.: 441,307

[22] Filed: Nov. 12, 1982

[51] Int. Cl.³ .............................................. C08G 63/08
[52] U.S. Cl. ................................ 528/354; 128/92 C; 128/335; 128/335.5; 525/408; 528/361
[58] Field of Search ............... 528/354, 361; 525/408, 525/450; 128/92 C, 335, 335.5, 348

[56] References Cited

U.S. PATENT DOCUMENTS

| | | | |
|---|---|---|---|
| 2,917,410 | 12/1959 | Vitalis | 117/138.8 |
| 3,636,956 | 1/1972 | Schnieder | 128/333.5 |
| 3,784,585 | 1/1974 | Schmitt et al. | 528/303 X |
| 4,048,256 | 9/1977 | Casey et al. | 260/860 |
| 4,243,775 | 1/1981 | Rosensaft et al. | 525/415 |

OTHER PUBLICATIONS

Reed et al., "Trans. Am. Soc. Artif. Intern. Organs", 1977, p. 109, *Biodegradable Elastomeric Biomaterials-Polyethylene Oxide/Polyethylene Terephthalate Copolymers.*

*Primary Examiner*—Earl A. Nielsen
*Attorney, Agent, or Firm*—Charles F. Costello, Jr.; Alphonse R. Noë

[57] ABSTRACT

Poly(glycolic acid)/poly(oxyalkylene) ABA triblock copolymers having the following formula:

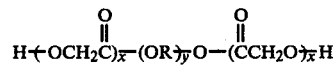

and wherein x and y have values which correspond to a total polyglycolide content of about 75 to 95 weight percent and a total polyoxyalkylene content of about 5 to 25 weight percent. The copolymers are useful for manufacturing fibers possessing a sufficiently low modulus of elasticity to permit their use as absorbable sutures having the requisite flexibility for use in monofilament form. A process of preparation involves purifying the hydroxyl-ended poly(oxyalkylene) and allowing it to react with glycolide to produce an ABA triblock copolymer of extrusion grade in which A represents a polyglycolic acid block and B represents a poly(oxyalkylene) block.

13 Claims, No Drawings

POLY(GLYCOLIC ACID)/POLY(OXYETHYLENE) TRIBLOCK COPOLYMERS AND METHOD OF MANUFACTURING THE SAME

CROSS REFERENCE TO RELATED APPLICATIONS

U.S. patent application Ser. No. 441,306 filed Nov. 12, 1982, assigned to the assignee of the present application discloses poly(glycolic acid)/poly(oxyalkylene) block copolymers manufactured by the transesterification of polyglycolic acid with an hydroxyl-ended poly(oxyalkylene) followed by the addition of an aromatic orthocarbonate to increase the degree of polymerization. The copolymers produced are, it is theorized, multiblocks having the structure $(AB)_n$ in which A and B are as defined above.

BACKGROUND OF THE INVENTION

This invention relates to copolymers based on poly(-glycolic acid), and methods of manufacturing the same, useful in the production of flexible, absorbable surgical articles including monofilament sutures or ligatures.

Synthetic absorbable sutures manufactured from polyglycolic acid are well known and have met with commercial success. Generally, such sutures are manufactured, sold and used as braids. However, some surgeons prefer the suturing characteristics of a monofilament suture. It has long been recognized that a need exists for an absorbable monofilament suture which exhibits the advantageous properties of strength, flexibility and absorbability possessed by polyglycolic acid braided sutures.

There have been various prior art suggestions for modifying polyglycolic acid, such as by copolymerization of glycolide monomer with other monomers, to produce a polymer possessing the requisite properties desired in a monofilament suture. For example, U.S. Pat. No. 4,243,775, Rosensaft and Webb, assigned to the assignee of the present invention, discloses a polymer material useful for forming both an absorbable braided suture and, under certain conditions, flexible monofilament sutures with extended strength retention. That patent discloses the sequential addition of a cyclic ester monomer, such as a lactide, lactone, oxalate or carbonate, to glycolide monomer in the copolymerization process. Triblock copolymers with lactic acid units predominantly on both ends of a glycolide polymer chain are disclosed as are copolymers of trimethylene carbonate and glycolide and monofilament sutures made therefrom.

Other copolymers for use as bioabsorbable materials have been disclosed. U.S. Pat. No. 4,048,256, assigned to the assignee of the present invention, discloses a normally solid bioabsorbable hydrolyzable polymeric reaction product of a polyglycolic acid composition and a polyester of diglycolic acid and an unhindered glycol. Copolymers of l(−)lactide with glycolide have also been used as suture material as disclosed in U.S. Pat. No. 3,636,956. Polyethylene oxide/polyethylene terephthalate copolymers have been disclosed as biodegradable elastomeric biomaterials in Reed, et al., "Trans. Am. Soc. Artif. Intern. Organs", 1977, page 109. The production of copolymers based on monomers formed from lactic acid or glycolic acid has been known for nonobiological purposes. U.S. Pat. No. 2,917,410 discloses the condensation of glycolic acid with a polyethylene glycol mixture to form an ester with an average molecular weight of 5105 for treating fabric for improved tear strength and abrasion resistance.

In order to produce an acceptable synthetic absorbable suture, monofilament fibers manufactured from a copolymer must meet certain requirements besides absorbability including good handling properties, adequate tensile and knot strength, avoidance of unfavorable tissue reactions, ability to be sterilized without significantly affecting desired properties and controllable uniformity in the desired properties. The acceptability of a suture is frequently determined by the Youngs modulus (a measurement of flexibility), the tensile strength and percent elongation at the breaking point, (a measure of extensibility).

SUMMARY OF THE INVENTION

The present invention provides a triblock copolymer of poly(glycolic acid) and poly(oxyalkylene) from which can be manufactured fibers possessing a sufficiently low modulus of elasticity to permit their use as absorbable surgical articles including the requisite flexibility for use in monofilament form. The process of preparing such triblock copolymers, according to the invention, provides extrusion molecular weight copolymers directly in a comparatively fast and procedurally simple manner.

The foregoing is achieved, according to the invention, by purifying the hydroxy-ended poly(oxyalkylene) and allowing it to react with glycolide to produce an ABA triblock copolymer of extrusion grade in which A represents a polyglycolic acid block and B represents a poly(oxyalkylene) block. The poly(oxyalkylene) serves both as a polymerization initiator for the two polyglycolic acid blocks and as a flexible middle block. The lower modulus of elasticity of the triblock copolymers enables their use in monofilament form such as absorbable monofilament sutures having increased flexibility compared to monofilaments of poly(glycolic acid) alone.

Thus, an object of this invention is the provision of a triblock copolymer of poly(glycolic acid)/poly(oxyalkylene) for producing absorabable surgical articles.

A further object of this invention is the provision of a method for producing a polyglycolic acid/polyoxyalkylene triblock copolymer which includes purification of polyoxyalkylene and reaction with glycolide which is comparatively procedurally simple and fast to carry out.

The triblock copolymers of this invention find advantageous utility in the manufacture of surgical articles and pharmaceutical composition as is known in the art for polymer absorbable in living animals. Thus, another object of this invention is the provision of a surgical article, a suture or ligature, particularly in the form of flexible monofilaments, or sutures in the form of a needle and suture combination, a surgical clip or staple, a surgical prosthesis, textile structures, couplings, tubes or other forms of support or a self-supporting film, hollow tube, beads or gel, containing a uniformly dispersed drug for controlled continuous administration, manufactured from a poly(glycolic acid)/poly(oxyalkylene) triblock copolymer.

The foregoing and other objects, features and advantages of this invention will be further apparent from the following description of preferred embodiments thereof and from the claims appended hereto.

DESCRIPTION OF THE PREFERRED EMBODIMENTS

The copolymers of this invention are ABA triblock copolymers having the following formula:

and wherein x and y have values which correspond to a total polyglycolide content of about 75 to 95 weight percent and a total polyoxyalkylene content of about 5 to 25 weight percent. In the above, the A block is represented by a poly(glycolic acid) while the B block is a poly(oxyalkylene). Preferably the B block is poly(oxyalkylene) however, it may comprise other poly(alkylene oxides) provided that they are hydroxyl-ended to initiate the glycolide polymerization and soluble in body fluids to enable the body to disperse the poly(alkylene oxide) segment once the copolymer has hydrolyzed. Examples of such poly(alkylene oxides) include polyols which produce linear polymers such as poly(oxyethylene) glycol and poly(oxypropylene)/poly(oxyethylene) glycols (block copolymers) and those which may produce branched polymers such as poly(oxypropylene) adducts of glycerol, poly(oxypropylene) adducts of trimethylolpropane, poly(oxypropylene)-poly(oxyethylene) adducts of trimethylolpropane, poly(oxypropylene) adducts of 1,2,6-hexanetriol, poly(oxypropylene) adducts of pentaerythritol, poly(oxypropylene) adducts of sorbitol, and poly(oxypropylene) adducts of sucrose. All the foregoing are commercially available under a variety of tradenames.

The poly(alkylene oxide) to be used in this invention is purified as follows. The poly(alkylene oxide) is dissolved in water to provide a 20 percent, by weight, solution. The aqueous solution is passed through a 25 cc packed column of Amberlite MB-3 cation/anion exchange resin to provide a contact area of 1 cc of resin per gram of poly(alkylene oxide). The resulting aqueous effluent is extracted with methylene chloride solvent, in an effluent/solvent ratio of 3/2 and the methylene chloride portion is then removed, under reduced pressure, to leave an oil. Acetone is added to the oil portion and the mixture is allowed to cool in order to solidify the poly(alkylene oxide) which is then recovered by filtration. The reference to poly(alkylene oxide) hereafter refers to such as so purified.

Monomers which can be used include not only glycolide but D,L-lactide, keto-1,4-dioxane, tetramethyl glycolide, ethylene oxalate and 2,5-diketomorpholine. Still other monomers can be used in combination with glycolide including: L-lactide, β-propiolactone, β-butyrolactone, γ-butyrolactone, delta-valerolactone, epsiloncaprolactone, pivalolactone, α,α-diethylpropiolactone, 6,8-dioxabicyclo[3,2,1]-octane-7-one, ethylene carbonate, 3-methyl-1,4-dioxane-2,5-dione, 3,3-dimethyl-1-4-dioxane-2,5-dione, trimethylene carbonate and intermolecular cyclic diesters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methylvaleric acid, α-hydroxyheptanoic acid, α-hydroxystearic acid, α-hydroxylignoceric acid and salicyclic acid.

The following examples illustrate preferred embodiments of the invention but are not to be taken as limiting.

EXAMPLE 1

A mixture of 2.6 g poly(oxyethylene) (Mol. Wt. 1540), 40.0 g glycolide and 0.8 ml of a solution of stannous chloride dihydrate in ether (2.5 mg/ml) was charged to a stirred reactor. The reaction mixture was evacuated to 0.25 mmHg and heated at 220° C. for 1¼ hr. Stirring was facilitated with a magnetic stirrer for the initial ¼ hr. The cooled, solidified polymer was crushed in a press, ground to 10 mesh in a Wiley mill and dried for 24 hours at 140° C., 0.25 mmHg. The inherent viscosity of the dried polymer was 0.60 (0.5% solution in hexafluoroacetone sesquihydrate (H.F.A.S.) at 30° C.).

EXAMPLE 2

The procedure of Example 1 was repeated using 3.4 g poly(oxyethylene) (Mol. Wt. 4000), 40.0 g glycolide and 0.8 ml of a solution of stannous chloride dihydrate in ether (2.5 mg/ml). The inherent viscosity of the ground and dried polymer was 0.75.

EXAMPLE 3

The procedure of Example 1 was followed using 6.8 g poly(oxyethylene) (Mol. Wt. 4000), 40.0 g glycolide and 0.8 ml of a solution of stannous chloride dihydrate in ether. The ground and dried polymer had an inherent viscosity of 0.61.

EXAMPLE 4

The procedure of Example 1 was followed using 5.1 g of poly(oxyethylene) (Mol. Wt. 6000), 40.0 g glycolide and 0.8 ml of a solution of stannous chloride dihydrate in ether (2.5 mg/ml). The inherent viscosity of the polymer was 1.03.

EXAMPLE 5

The procedure of Example 1 was followed using 10.3 g poly(oxyethylene) (Mol. Wt. 6000), 40.0 g glycolide and 0.8 ml of a solution of stannous chloride dihydrate in ether (2.5 mg/ml). An inherent viscosity of 0.82 was measured for the finished polymer.

EXAMPLE 6

A mixture of 3.4 g poly(oxyethylene) (Mol. Wt. 4000), 40.0 g glycolide and 0.8 ml of a solution of stannous chloride dihydrate in ether (0.2 mg/ml) was charged to a stirred reactor. After evacuating to 0.5 mmHg, the reactor was heated to 212° C. The temperature was raised to 227° C. over 1¼ hr. Stirring was facilitated with a magnetic stirrer for the initial ¼ hr. After maintaining a temperature of 227° C. for an additional 1¼ hr., the reaction mixture was cooled and the polymer was crushed and ground to 10 mesh in a Wiley Mill. After the polymer had been dried at 140° C., 1 mm Hg for 24 hr., the inherent viscosity was 0.61 (0.5% in H.F.A.S. at 30° C.).

EXAMPLE 7

A mixture of 13.6 g poly(oxyethylene) (Mol. Wt. 4000), 160.0 g glycolide and 3.2 ml of a solution of stannous chloride dihydrate in ether (2.5 mg/ml) was charged to a stirred reactor at 180° C. Under a stream of nitrogen and at an agitator speed of 60 RPM, the temperature was increased to 228° C. over ¼ hr. This temperature was maintained over the next 1¼ hr. at an agitator speed of 18 RPM. The polymer was discharged, cooled, ground to 10 mesh in a Wiley Mill and dried for 24 hrs. at 130°-175° C., 0.6-4.0 mm Hg.

EXAMPLE 8

A mixture of 17.3 g of poly(oxyethylene) (Mol. Wt. 6000), 135.0 g glycolide and 2.7 ml of a solution of stannous chloride dihydrate in ether (2.5 mg/ml) was charged to a reactor at 182° C. Under a stream of nitrogen and at an agitator speed of 60 RPM, the temperature was increased to 192° C. over ¼ hr. The agitator speed was reduced to 18 RPM and the temperature was increased to 227° C. over the next ¾ hr. After maintaining this temperature for an additional ¼ hr., the polymer was discharged, cooled, ground to a 10 mesh in a Wiley Mill and dried for 24 hrs. at 130°-175° C., 0.4-4,0 mm Hg.

EXAMPLE 9

The procedure of Example 6 was followed using 41.2 g poly(oxyethylene) (Mol. Wt. 6000), 160.0 g glycolide and 3.2 ml of a solution of stannous chloride dihydrate in ether (2.5 mg/ml).

A comparison of the physical properties of the triblock copolymer prepared according to Examples 7, 8 and 9 is set forth in Table I.

TABLE I

Physical Properties of PGA/POE Block Copolymers

| Example | Mol. Wt. of POE | Wt. % POE charged | Wt. % POE By NMR | $\eta_{inh}^1$ (H.F.A.S.) | $T_g^2$ | $T_m^3$ |
|---|---|---|---|---|---|---|
| 7 | 4000 | 7.8 | 6.7 | 0.73 | 33 | 221° |
| 8 | 6000 | 11.4 | 10.7 | 0.82 | 39 | 222° |
| 9 | 6000 | 20.5 | 20.2 | 0.64 | — | 221° |

[1] At 0.5%, 30° C.
[2] By DSC
[3] Peak Temperature determined by DSC

EXAMPLE 10

Copolymer from Example 7 was extruded in a CSI-Max Extruder and drawn 4.6X on a hot air single zone drawing unit at 45° C.

EXAMPLE 11

Copolymer from Example 8 was extruded in a CSI-Max Extruder and drawn 4.8X on a hot air single zone drawing unit at 50° C.

EXAMPLE 12

Copolymer from Example 9 was extruded in a CSI-Max Extruder and drawn 4.3X on a hot bar at 45° C.

The straight pull tensile strength, modulus of elasticity and straight pull elongation at break were measured for the triblock copolymer of Examples 11, 12 and 13 and compared to polyglycolic acid control monofilaments. The results, set forth in Table II, show that the triblock copolymers exhibit increased flexibility.

TABLE II

Fibers Prepared From PGA/POE Block Copolymers

| Example | Dia. (mm) | Draw Ratio | SP(psi)[1] | Modulus (psi)[2] | % E[3] |
|---|---|---|---|---|---|
| 10 | 0.116 | 4.6 | 70,000 | $1.3 \times 10^6$ | 25 |
| PGA Control | 0.099 | 5.4 | 127,000 | $2.4 \times 10^6$ | 35 |
| 11 | 0.202 | 4.8 | 84,000 | $1.4 \times 10^6$ | 31 |
| PGA Control | 0.158 | 6.0 | 107,000 | $2.1 \times 10^6$ | 57 |
| 12 | 0.140 | 4.3 | 45,000 | $0.55 \times 10^6$ | 33 |

[1] Straight Pull Tensile Strength
[2] Tensile Modulus
[3] % Elongation at Break The in vitro hydrolysis of the triblock copolymers of Examples 10, 11 and 12 was determined by placing monofilaments in a buffered solution at 39° C. and measuring the fiber tensile strength at various times. The results, expressed as a percentage of the intial fiber tensile strength, are set forth in Table III.

TABLE III

In Vitro Hydrolysis of PGA/POE Block Copolymers

| | Initial Strength Retained, % | | |
|---|---|---|---|
| Example | 4 days | 7 days | 10 days |
| 10 | — | 19 | 1.5 |
| 11 | 46 | 8 | 0.5 |
| 12 | 107 | 5 | 0 |
| PGA Control | — | 92,63 | 63,47 |

The preferred area for use of the triblock copolymers of the present invention is in the manufacture of synthetic absorbable surgical articles such as monofilament sutures or ligatures. The in vivo absorption of pressed strips of the triblock copolymer of Examples 4, 5, 7, 8 and 9 was determined. The strips were prepared by reprecipitating the polymers with methanol from hexafluoroacetone sesquihydrate (H.F.A.S.), pressing in a hydraulic press at 1600 lb/in$^2$ for one minute and sterilizing the resulting compacted strips. The strips were then implanted subcutaneously in rabbits and the extent of absorption was visually estimated at various times. Examination of the implant sites carried out at 30, 45 and 60 days indicated complete absorption by 60 days. The results are set forth in Table IV.

TABLE IV

In Vivo Absorption of PGA/POE Block Copolymer Pressed Strips

| | Composition as charged | Time Days | | |
|---|---|---|---|---|
| Example | PGA/POE | 30 | 45 | 60 |
| 4 | 89/11 | 50 | 100 | 100 |
| 5 | 80/20 | 75 | 95 | 100 |
| 7 | 92/8 | 75-95 | 95-100 | 100 |
| 8 | 89/11 | 100 | 95 | 100 |
| 9 | 80/20 | 75-90 | 100 | 95-100 |
| PGA | 100/0 | 90 | 95 | 100 |

The surgical articles are fabricated from the triblock copolymer, and subsequently sterilized, using conventionally employed procedures. The resulting surgical articles are employed in a conventional manner using known techniques.

We claim:

1. A triblock copolymer useful in fiber form for the manufacture of bioabsorbable surgical articles comprising the formula:

wherein R represents an alkylene, x and y have values which correspond to a total polyglycolide content of about 75 to 95 weight percent and a total polyoxyalkylene content of about 5 to 25, weight percent.

2. A triblock copolymer as claimed in claim 1 wherein R is poly(oxyethylene).

3. A surgical article manufactured from a triblock copolymer as claimed in claim 1.

4. A suture or ligature manufactured from a triblock copolymer as claimed in claim 1.

5. A surgical article as claimed in claim 3 selected from the group consisting of a suture, ligature, needle and suture combination, surgical clip, surgical staple, surgical prosthesis, textile structure, coupling, tube, and support.

6. A method for preparing extrusion weight triblock copolymers having the formula:

wherein R represents an alkylene, x and y have values which correspond to a total polyglycolide content of about 75 and 95 weight percent and a total polyoxyalkylene content of about 5 to 25 weight percent, comprising reacting purified hydroxyl-ended poly(alkylene oxide) with glycolide by charging the respective constituents to a stirred reactor in the presence of stannous chloride dihydrate, heating at a temperature of 220°–228° C. for a period of time sufficient to achieve the desired reaction, followed by cooling and recovering a solidified copolymer having an intrinsic viscosity of at least 0.60.

7. A method as claimed in claim 6 wherein the purified hydroxyl-ended poly(alkylene oxide) is obtained by passing an aqueous solution of the poly(alkylene oxide) through an ion exchange resin bed, extracting the resulting effluent with a solvent, removing the solvent fraction, adding acetone to the remaining fraction and allowing it to cool to provide solidified poly(alkylene oxide) and filtering to recover the same.

8. A method for manufacturing a surgical article comprising extruding the triblock copolymer produced by the method as claimed in claim 6.

9. A bioabsorbable surgical article manufactured from a copolymer in fiber form, said copolymer made according to a method claimed in claim 7.

10. A bioabsorbable flexible monofilament suture or ligature manufactured from copolymer made according to a method claimed in claim 6.

11. A surgical article as claimed in claim 9 selected from the group consisting of a suture, ligature, needle and suture combination, surgical clip, surgical staple, surgical prosthesis, textile structure, coupling, tube, and support.

12. A triblock copolymer for use in manufacturing absorbable surgical articles comprising the formula:

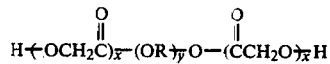

wherein R represents an alkylene, x and y have values which correspond to a total polyglycolide content of about 75 and 95 weight percent and a total polyoxyalkylene content of about 5 to 25 weight percent, and having, as an extruded fiber, a straight pull tensile strength in excess of 40,000 psi and a modulus less than $2.5 \times 10^6$ psi.

13. A triblock copolymer as claimed in claim 12 having an in vivo absorbability, as measured by subcutaneous implantation in rabbits, of 100 percent after 60 days.

* * * * *